United States Patent
Driver et al.

(10) Patent No.: US 8,105,481 B2
(45) Date of Patent: Jan. 31, 2012

(54) REDUCTION OF ORGANIC HALIDE CONTAMINATION IN HYDROCARBON PRODUCTS

(75) Inventors: Michael S. Driver, San Francisco, CA (US); Howard S. Lacheen, Richmond, CA (US); Mitra A. Hosseini, Dublin, CA (US)

(73) Assignee: Chevron U.S.A. Inc., San Ramon, CA (US)

(*) Notice: Subject to any disclaimer, the term of this patent is extended or adjusted under 35 U.S.C. 154(b) by 363 days.

(21) Appl. No.: 11/960,506

(22) Filed: Dec. 19, 2007

(65) Prior Publication Data

US 2009/0163759 A1    Jun. 25, 2009

(51) Int. Cl.
*C10G 25/05* (2006.01)
(52) U.S. Cl. .......... 208/262.1; 585/820; 95/101; 95/102
(58) Field of Classification Search .......... None
See application file for complete search history.

(56) References Cited

U.S. PATENT DOCUMENTS

| | | | | |
|---|---|---|---|---|
| 3,383,430 | A | * | 5/1968 | Hutson, Jr. et al. .......... 570/252 |
| 3,862,900 | A | * | 1/1975 | Reusser .......... 208/262.1 |
| 4,122,245 | A | | 10/1978 | Nardi et al. |
| 5,453,113 | A | * | 9/1995 | Zarchy et al. .......... 95/41 |
| 5,731,101 | A | | 3/1998 | Sherif et al. |
| 5,750,455 | A | | 5/1998 | Chauvin et al. |
| 5,952,541 | A | * | 9/1999 | Ou et al. |
| 6,028,024 | A | | 2/2000 | Hirschauer et al. |
| 6,235,959 | B1 | | 5/2001 | Hirschauer et al. |
| 6,797,853 | B2 | | 9/2004 | Houzvicka et al. |
| 7,432,409 | B2 | * | 10/2008 | Elomari et al. .......... 585/722 |
| 2003/0060359 | A1 | | 3/2003 | Olivier-Bourbigou et al. |
| 2004/0077914 | A1 | | 4/2004 | Zavilla et al. |
| 2004/0133056 | A1 | | 7/2004 | Liu et al. |
| 2005/0256351 | A1 | * | 11/2005 | Birke et al. .......... 585/10 |
| 2006/0063945 | A1 | * | 3/2006 | Wasserscheid et al. .......... 554/85 |

OTHER PUBLICATIONS

A.K. Roebuck and B.L. Evering; Isobutane-Olefin Alkylation with Inhibited Aluminum Chloride Catalysts; p. 77; Ind. Eng. Chem. Prod. Res. Develop., vol. 9, No. 1, Mar. 1970.

Yves Chauvin, Andre Hirchauer, Helene Olivier; Alkylation of isobutane with 2-butene using 1-butyl-3-methylimidazolium chloride-aluminium chloride molten salts as catalysts; Journal of Molecular Catalysis 92 (1994) 155-165; Elsevier science B.V., Netherlands.

Murate G. Suer, Zissis Dardas, Yi. H. Ma and William R. Moser; An in Situ CIR-FTIR Study of n-Heptane Cracking over a Commercial Y-Type Zeolite under Subcritical and Supercritical Conditions; Journal of Catalysis 162, 320-326 (1996).

Rodrigo J. Correa and Claudio J.A. Mota; Sn2, E2 reactions of butylchlorides on NaY zeolite; A potential method for studying the formation and reactivity of alkoxy species on the zeolite surface; Phys. Chem. Chem. Phys., 2002, 4, 4268-4274.

Peter Wasserscheid, Thomas Welton; Ionic Liquids in Synthesis; 2003; p. 275; Wiley-VCH Verlag GmbH & Co. KGaA.

* cited by examiner

*Primary Examiner* — Tam M Nguyen

(74) *Attorney, Agent, or Firm* — Steven H. Roth; Susan M. Abernathy

(57) ABSTRACT

A method for reducing halide concentration in a hydrocarbon product having an organic halide content from 50 to 4000 ppm which is made by a hydrocarbon conversion process using an ionic liquid catalyst comprising a halogen-containing acidic ionic liquid comprising contacting at least a portion of the hydrocarbon product with at least one molecular sieve having pore size from 4 to 16 Angstrom under organic halide absorption conditions to reduce the halogen concentration in the hydrocarbon product to less than 40 ppm is disclosed.

30 Claims, No Drawings

REDUCTION OF ORGANIC HALIDE CONTAMINATION IN HYDROCARBON PRODUCTS

FIELD OF THE INVENTION

The present invention relates to methods for reducing organic halide concentration in a hydrocarbon product made by a hydrocarbon conversion process using an ionic liquid catalyst comprising a halogen-containing acidic ionic liquid.

BACKGROUND OF THE INVENTION

Ionic liquids are liquids that are composed entirely of ions. The so-called "low temperature" Ionic liquids are generally organic salts with melting points under 100 degrees C., often even lower than room temperature. Ionic liquids may be suitable for example for use as a catalyst and as a solvent in alkylation and polymerization reactions as well as in dimerization, oligomerization, acetylation, metatheses, and copolymerization reactions.

One class of ionic liquids is fused salt compositions, which are molten at low temperature and are useful as catalysts, solvents and electrolytes. Such compositions are mixtures of components which are liquid at temperatures below the individual melting points of the components.

Ionic liquids can be defined as liquids whose make-up is entirely comprised of ions as a combination of cations and anions. The most common ionic liquids are those prepared from organic-based cations and inorganic or organic anions. The most common organic cations are ammonium cations, but phosphonium and sulphonium cations are also frequently used. Ionic liquids of pyridinium and imidazolium are perhaps the most commonly used cations. Anions include, but not limited to, $BF_4^-$, $PF_6^-$, haloaluminates such as $Al_2Cl_7^-$ and $Al_2Br_7^-$, $[(CF_3SO_2)_2N]^-$, alkyl sulphates ($RSO_3^-$), carboxylates ($RCO_2^-$) and many other. The most catalytically interesting ionic liquids for acid catalysis are those derived from ammonium halides and Lewis acids (such as $AlCl_3$, $TiCl_4$, $SnCl_4$, $FeCl_3$ . . . etc). Chloroaluminate ionic liquids are perhaps the most commonly used ionic liquid catalyst systems for acid-catalyzed reactions.

Examples of such low temperature ionic liquids or molten fused salts are the chloroaluminate salts. Alkyl imidazolium or pyridinium chlorides, for example, can be mixed with aluminum trichloride ($AlCl_3$) to form the fused chloroaluminate salts. The use of the fused salts of 1-alkylpyridinium chloride and aluminum trichloride as electrolytes is discussed in U.S. Pat. No. 4,122,245.

Other examples of ionic liquids and their methods of preparation may also be found in U.S. Pat. Nos. 5,731,101; 6,797,853 and in U.S. Patent Application Publications 2004/0077914 and 2004/0133056.

The alkylation of isobutane with butenes and ethylene in ionic liquids has been described in U.S. Pat. Nos. 5,750,455; 6,028,024; and 6,235,959 and open literature (*Journal of Molecular Catalysis*, 92 (1994), 155-165; "*Ionic Liquids in Synthesis*", P. Wasserscheid and T. Welton (eds.), Wiley-VCH Verlag, 2003, pp 275).

Use of molecular sieves as adsorbents has been discussed in the literature. The interaction of butyl chlorides with NaY zeolite have been reported in Suer et al; *Journal of Catalysis*, 1996, 162, 320-326 and Correa et al; *Phys. Chem. Chem. Phys.*, 2002, 4, 4268-4274.

In general, conversion of light paraffins and light olefins to more valuable cuts is very lucrative to the refining industries. This has been accomplished by alkylation of paraffins with olefins, and by polymerization of olefins. One of the most widely used processes in this field is the alkylation of isobutane with $C_3$ to $C_5$ olefins to make gasoline cuts with high octane number using sulfuric and hydrofluoric acids. This process has been used by refining industries since the 1940's. The process was driven by the increasing demand for high quality and clean burning high-octane gasoline.

Alkylate gasoline is a high quality and efficient burning gasoline that constitutes about 14% of the gasoline pool. Alkylate gasoline is typically produced by alkylating refineries isobutane with low-end olefins (mainly butenes). Currently, alkylates are produced by using HF and $H_2SO_4$ as catalysts. Although these catalysts have been successfully used to economically produce the best quality alkylates, the need for safer and more environmentally friendly catalysts systems has become an issue to the industries involved.

SUMMARY OF THE INVENTION

The present invention relates to methods for reducing organic halide concentration in hydrocarbon products having an organic halide content from 50 to 4000 ppm which are made by hydrocarbon conversion processes using halogen-containing acidic ionic liquid catalysts. The methods comprise contacting at least a portion of the hydrocarbon product with a molecular sieve having pore sizes from 4 to 16 Angstrom under organic halide absorption conditions to reduce the halogen concentration in the hydrocarbon products to less than 40 ppm.

DETAILED DESCRIPTION

Hydrocarbon conversion processes using a halogen-containing acidic ionic liquid catalyst which will generally produce a hydrocarbon product having an organic halide impurity content from 50 to 4000 ppm. Examples of such processes include alkylation of paraffins, alkylation of aromatics, polymerization, dimerization, oligomerization, acetylation, metatheses, copolymerization, isomerization, olefin hydrogenation, hydroformylation. The presence of organic halides in such products may be undesirable. The present process can be used to reduce the organic halide concentration is such hydrocarbon products.

The present process is being described and exemplified herein in large part by reference to alkylation processes using certain specific ionic liquid catalysts, but such description is not intended to limit the scope of the invention. The organic halide reduction processes described herein may be used for any hydrocarbon product having an organic halide content from 50 to 4000 ppm which are made by hydrocarbon conversion processes using ionic liquid catalysts comprising halogen-containing acidic ionic liquids as will be appreciated by those persons having ordinary skill based on the teachings, descriptions and examples included herein.

In one aspect the present process relates to an alkylation process comprising contacting a hydrocarbon mixture comprising at least one olefin having from 2 to 6 carbon atoms and at least one isoparaffin having from 3 to 6 carbon atoms with a halogen-containing acidic ionic liquid catalyst under alkylation conditions.

In general, a strongly acidic ionic liquid is necessary for paraffin alkylation, e.g. isoparaffin alkylation. In that case, aluminum chloride, which is a strong Lewis acid in a combination with a small concentration of a Bronsted acid, is a preferred catalyst component in the ionic liquid catalyst scheme.

As noted above, the acidic ionic liquid may be any acidic ionic liquid. In one embodiment, the acidic ionic liquid is a chloroaluminate ionic liquid prepared by mixing aluminum trichloride (AlCl$_3$) and a hydrocarbyl substituted pyridinium halide, a hydrocarbyl substituted imidazolium halide, trialkylammonium hydrohalide or tetraalkylammonium halide to make an ionic liquid of the general formulas A, B, C and D, respectively,

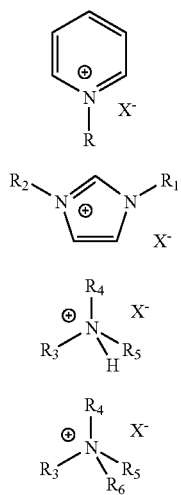

where R=H, methyl, ethyl, propyl, butyl, pentyl or hexyl group and X is a haloaluminate and preferably a chloroaluminate, and R$_1$ and R$_2$=H, methyl, ethyl, propyl, butyl, pentyl or hexyl group and where R$_1$ and R$_2$ may or may not be the same, and R$_3$, R$_4$, and R$_5$ and R$_6$=methyl, ethyl, propyl, butyl, pentyl or hexyl group and where R$_3$, R$_4$, R$_5$ and R$_6$ may or may not be the same.

The acidic ionic liquid is preferably selected from the group consisting of 1-butyl-4-methyl-pyridinium chloroaluminate, 1-butyl-pyridinium chloroaluminate, 1-butyl-3-methyl-imidazolium chloroaluminate and 1-H-pyridinium chloroaluminate. In a process according to the invention an alkyl halide may optionally be used as a promoter.

An alkyl halide is optionally added to the ionic liquid catalyst and acts to promote the alkylation by reacting with aluminum chloride to form the prerequisite cation ions in similar fashion to the Friedel-Crafts reactions. The alkyl halides that may be used include alkyl bromides, alkyl chlorides and alkyl iodides. Preferred are isopentyl halides, isobutyl halides, butyl halides, propyl halides and ethyl halides. Alkyl chloride versions of these alkyl halides are preferable when chloroaluminate ionic liquids are used as the catalyst systems. Other alkyl chlorides or halides having from 1 to 8 carbon atoms may be also used. The alkyl halides may be used alone or in combination.

A metal halide may be employed to modify the catalyst activity and selectivity. The metal halides most commonly used as inhibitors/modifiers in aluminum chloride-catalyzed olefin-isoparaffin alkylations include NaCl, LiCl, KCl, BeCl$_2$, CaCl$_2$, BaCl$_2$, SrCl$_2$, MgCl$_2$, PbCl$_2$, CuCl, ZrCl$_4$ and AgCl, as described by Roebuck and Evering (Ind. Eng. Chem. Prod. Res. Develop., Vol. 9, 77, 1970). Preferred metal halides are CuCl, AgCl, PbCl$_2$, LiCl, and ZrCl$_4$.

HCl or any Bronsted acid may be employed as co-catalyst to enhance the activity of the catalyst by boasting the overall acidity of the ionic liquid-based catalyst. The use of such co-catalysts and ionic liquid catalysts is disclosed in U.S. Published Patent Application Nos. 2003/0060359 and 2004/0077914. Other co-catalysts that may be used to enhance the activity include IVB metal compounds preferably IVB metal halides such as ZrCl$_4$, ZrBr$_4$, TiCl$_4$, TiCl$_3$, TiBr$_4$, TiBr$_3$, HfCl$_4$, HfBr$_4$ as described by Hirschauer et al. in U.S. Pat. No. 6,028,024.

For example, in the process of producing alkylate hydrocarbon gasoline using haloaluminate ionic liquid catalysts, trace amounts of organic halides are found in the alkylate hydrocarbon. Removal of organic halides from gasoline is desirable to meet product specifications. Analogous results will occur, of course, when ionic liquid catalysts containing halides other than chlorides are used.

In an embodiment in which the ionic liquid catalyst contains chlorides, the organic halides that contaminate the resulting product are organic chlorides. The chloride content in an alkylate hydrocarbon stream prepared using a chloroaluminate ionic liquid catalyst is generally from 50 ppm to 4000 ppm. Removal of trace organic chlorides from alkylate is also desirable since organic chlorides may generate corrosive or harmful material such as HCl or dioxins during combustion.

In the present process, a molecular sieve is used to absorb organic halides and remove them from the hydrocarbon product. Molecular sieves useful in this process of absorption are selected from the group consisting of large pore zeolites, intermediate pore size zeolites and small pore zeolites.

Zeolites are aluminosilicates with a one to three dimensional structure forming channels and cages with molecular dimensions. The aluminium atoms are tetracoordinated, developing a negative charge on the structure, which is compensated by the extra framework cations. The amount of aluminum in zeolite can be varied widely ranging SiO$_2$/Al$_2$O$_3$ molar ratio of 1 to 10,000.

Large pore, intermediate pore or small pore molecular sieves having pore sizes from 4 to 16 Angstrom can be used as absorbents to reduce the organic halide content in the alkylate. Large pore molecular sieves include Zeolite X, Zeolite Y, USY zeolite, Mordenite, ALPO-5, SAPO-5, Beta, ZSM-12, MCM-22, MCM-36, MCM-68, ITQ-7, ITQ-10, ITQ-14, SSZ-24, SSZ-31, SSZ-33, SSZ-48, SSZ-55, SSZ-59 and SSZ-60. Intermediate pore size zeolite includes ZSM-5, ZSM-11, ZSM-22, ZSM-35, ALPO-11, SAPO-11, SSZ-25, SSZ-32, SSZ-35, SSZ-41, and SSZ-44. Small pore molecular sieves include Zeolite A, SSZ-16, SSZ-39, and SSZ-52. These materials can have different cations. Most common extra framework cations are sodium, potassium, cesium, calcium, magnesium and barium.

The large pore, intermediate pore and small pore molecular sieves can be used alone or as mixtures. For example, it is possible to use a mixture of a large pore size zeolite and a small pore size zeolite as well as mixtures of different small pore zeolites.

In one embodiment of the present process, The organic halogen-containing alkylate which contains organic halides is contacted with molecular sieve under absorption conditions which can include a temperature of from 32° F. to 1000° F., pressure of 1 psi to 1000 psi with a liquid hourly space velocity (LHSV) between 0.1 hr$^{-1}$ and 40 hr$^{-1}$. In one embodiment the molecular sieve is maintained at room temperature and pressure. Processes in accordance with the invention may be conducted as batch, semi-continuous or continuous processes.

Organic chloride levels in alkylate hydrocarbon product can be measured after the absorption process. In an embodiment, the organic chloride content in the alkylate hydrocarbon product is less than 40 ppm. In another embodiment, the organic chloride content in the alkylate hydrocarbon product is less than 10 ppm.

The molecular sieve is effective in removing the organic chloride until it reaches its full absorption capacity for organic chloride. Different zeolites or molecular sieves have different absorption capacities for organic chloride. It is generally preferred to have material with high organic chloride absorption capacity since high capacity material can treat larger volume of organic chloride containing gasoline.

After the molecular sieve reaches its full capacity for organic chloride absorption and can not absorb any more organic chloride, the molecular sieve can be optionally regenerated or reactivated for multiple cycle use. The reactivation procedure can include stopping contacting the alkylate containing gasoline with the molecular sieve material, and then raising the bed temperature with flow of a desorption medium. Desorption mediums that can be used include $N_2$ gas, $H_2$ gas, air, $CO_2$ in gas or in supercritical liquid state, and C1-C10 light hydrocarbons, preferably free of organic chloride. Desorption conditions include a temperature of from 200° F. to 1000° F., pressure of 1 psi to 1000 psi with a gas hourly space velocity (GHSV) between 1 $hr^{-1}$ and 10,000 $hr^{-1}$ or a liquid hourly space velocity (LHSV) between 0.1 $hr^{-1}$ and 40 $hr^{-1}$. After completion of desorption, the molecular sieve is reactivated and ready for another cycle of organic chloride absorption.

EXAMPLES

The following Examples are illustrative of the present invention, but are not intended to limit the invention in any way beyond what is contained in the claims which follow.

Zeolites of different compositions and pore sizes were tested. The USY zeolite, NaX zeolite are large pore molecular sieves containing three-dimensional network of 13 Å diameter supercages with 7.2 Å diameter pore diameter. Cs exchanged USY was studied and showed that zeolites with varying cations are effective in organic chloride removal. NaA zeolite is a small pore molecular sieve containing two-dimensional network of 4 Å diameter pore channels. The organic halide removal performance of these zeolites was compared with silica-alumina which contains comparable total pore volume to USY except that the pores in silica-alumina are mainly macropores (>30 Å pore diameter) and silica-alumina contains very little micropores (<20 Å pore diameter)

The NaX, USY, NaA, and silica-alumina were purchased. CsUSY was prepared by exchange of USY with Cs. All these materials were calcined at 538° C. for 3 hours under flowing dry air to remove any absorbed moisture. Then the materials were cooled under N2 and stored in air-tight containers before the absorption experiment.

Example 1

Chloride Reduction in Alkylate Hydrocarbon Using Various Adsorption Material

In a closed container, 0.5 g of absorption material and 50 mL of gasoline containing organic chloride were charged. The mixture was shaken vigorously to ensure uniform mixing for 30 minutes. Then the mixture is allowed to settle to separate the alkylate gasoline from the solid absorbent material. Gasoline samples before and after absorption were compared to determine effectiveness of absorption material. The results are summarized in Table 1.

TABLE 1

Comparison of Organic Chloride Uptake by Zeolite vs. Amorphous Material

| Absorption Material | Cl (ppm) in As-Alkylated Gasoline | Cl (ppm) in Gasoline, After Absorption | Cl Reduction, % | Comment |
| --- | --- | --- | --- | --- |
| Silica-alumina | 1286 | 1012 | 21.3 | Base case |
| USY | 1286 | 37 | 97.1 | Invention |
| NaX | 880 | <5 | 99+ | Invention |

The above results indicate that NaX and USY zeolites gave far better performance than amorphous silica-alumina. Our results clearly showed that micropore containing molecular sieve material is much preferred over amorphous materials.

Example 2

Chloride Absorption Capacity of Various Adsorption Material

Table 2 summarizes the absorption capacity of the different materials. In these examples, different amounts of the absorption material were added to 50 mL of gasoline containing alkyl chloride The chloride levels in the alkylate hydrocarbon gasoline and the alkylate hydrocarbon product were measured. Then the maximum uptake capacity of organic chloride per gram of absorbent material was calculated.

TABLE 2

Organic Chloride Uptake Capacity of Various Materials

| Absorption Material | Absorption Capacity, g Cl/g absorbent | Comment |
| --- | --- | --- |
| Silica-alumina | 0.01 | Base case |
| NaA | 0.06 | Invention |
| NaX | 0.16 | Invention |
| USY | 0.07 | Invention |
| Cs exchanged USY | 0.05 | Invention |

The above data indicate micropore containing zeolite materials have far superior absorption capacity for organic chloride that mesoporous silica-alumina material.

Example 3

Continuous Organic Chloride Removal Process

A ⅜" O.D. reactor tube was charged with a 12 cc of NaX molecular sieve sized to −24/+40 diluted with 6 cc of 90 grit silicon carbide. The NaX was dried by heating to 600° F. for a minimum of 1 hour under a $N_2$ flow. The reactor was then allowed to cool to room temperature (approximately 70° F.). Alkylate gasoline with a chloride level between 50 ppm and 900 ppm was then passed over the absorption material at room temperature at a linear hourly space velocity (LHSV) between 1 $hr^{-1}$ and 10 $hr^{-1}$. The reactor effluent was collected and analyzed by X-ray Fluorescence Spectrometry (XRF) to measure the chloride level. The alkylate gasoline was fed to the unit until breakthrough of organic chloride was observed, and absorption capacity was calculated.

During the absorption period, the NaX molecular sieve showed a chloride absorption capacity of 0.1 g chloride/g NaX. Analysis of the reactor effluent by gas chromatography showed no degradation of the alkylate gasoline during the absorption process.

Example 4

Reactivation of Molecular Sieve Using Desorption Gas

The NaX material fully saturation with chloride from Example 3 was reactivated per procedure below to recover the absorption capacity.

First, the flow of alkylate stream containing organic chloride was stopped. Then the reactor was heated 600° F. under N$_2$ flow overnight. The next day, NaX was cooled to room temperature, and then resumed process of alkylate stream containing organic chloride per Example 3. The capacity of the NaX was recovered from 0 to 0.08 g chloride/g NaX by this reactivation process.

What is claimed is:

1. An alkylation process comprising contacting a first hydrocarbon feed comprising at least one olefin having from 2 to 6 carbon atoms and a second hydrocarbon feed comprising at least one isoparaffin having from 4 to 6 carbon atoms with a halogen-containing acidic ionic liquid catalyst under alkylation conditions to produce an alkylate gasoline having an organic halide content from 50 to 4000 ppm and contacting at least a portion of the alkylate gasoline with at least one molecular sieve having a pore size from 4 to 16 Angstrom under organic halide absorption conditions, whereby the organic halide is absorbed during the contacting to reduce the organic halide content by 97.1% or greater in the alkylate gasoline to an amount less than 40 ppm.

2. The alkylation process according to claim 1, wherein the molecular sieve is selected from the group consisting of large pore size zeolites, intermediate pore size zeolites, small pore size zeolites and their mixtures.

3. The alkylation process according to claim 1, wherein the molecular sieve is selected from the group consisting of Zeolite X, Zeolite Y, USY zeolite, Mordenite, ALPO-5, SAPO-5, Beta, ZSM-12, MCM-22, MCM-36, MCM-68, ITQ-7, ITQ-10, ITQ-14, SSZ-24, SSZ-31, SSZ-33, SSZ-48, SSZ-55, SSZ-59, SSZ-60 and their mixtures.

4. The alkylation process according to claim 1, wherein the molecular sieve is selected from the group consisting of ZSM-5, ZSM-11, ZSM-22, ZSM-35, ALPO-11, SAPO-11, SSZ-25, SSZ-32, SSZ-35, SSZ-41, SSZ-44 and their mixtures.

5. The alkylation process according to claim 1, wherein the molecular sieve is selected from the group consisting of Zeolite A, SSZ-16, SSZ-39, SSZ-52 and their mixtures.

6. The alkylation process according to claim 1, wherein the ionic liquid catalyst used is N-butylpyridinium chloroaluminate.

7. The alkylation process according to claim 1, wherein the molecular sieve is reactivated and reused as the at least one molecular sieve.

8. The alkylation process according to claim 1, wherein the molecular sieve is NaX zeolite.

9. An alkylation process comprising contacting a first hydrocarbon feed comprising at least one olefin having from 2 to 5 carbon atoms and a second hydrocarbon feed comprising at least one isoparaffin having from 4 to 6 carbon atoms with a halogen-containing acidic ionic liquid catalyst under alkylation conditions to produce an alkylate having an organic halide content from 50 to 4000 ppm and contacting at least a portion of the alkylate with at least one molecular sieve having a pore size from 4 to 16 Angstrom under organic halide absorption conditions to reduce the organic halide content in the alkylate by 97.1% or greater to produce an alkylate hydrocarbon product with an organic chloride content less than 40 ppm; whereby the organic halide is absorbed during the contacting of the at least the portion of the alkylate with at least one molecular sieve and the alkylate hydrocarbon product is not degraded during the contacting.

10. The alkylation process according to claim 9, wherein the molecular sieve is selected from the group consisting of large pore size zeolites, intermediate pore size zeolites, small pore size zeolites and their mixtures.

11. The alkylation process according to claim 9, wherein the ionic liquid catalyst used is N-butylpyridinium chloroaluminate.

12. The alkylation process according to claim 9, wherein the molecular sieve is reactivated and reused as the at least one molecular sieve.

13. The alkylation process according to claim 9, wherein the alkylate hydrocarbon product comprises an alkylate gasoline.

14. The alkylation process of claim 9, wherein the at least one molecular sieve comprises a mixture of a large pore size zeolite and a small pore size zeolite.

15. The alkylation process of claim 9, wherein the at least one molecular sieve comprises a mixture of different small pore zeolites.

16. An alkylation process comprising contacting a first hydrocarbon feed comprising at least one olefin having from 2 to 6 carbon atoms and a second hydrocarbon feed comprising at least one isoparaffin having from 4 to 6 carbon atoms with a halogen-containing acidic ionic liquid catalyst under alkylation conditions to produce an alkylate having an organic halide content from 50 to 4000 ppm and contacting at least a portion of the alkylate with at least one molecular sieve under organic halide absorption conditions to reduce the organic halide content by 97.1% or greater to produce an alkylate gasoline with an organic chloride content less than 40 ppm; and wherein the alkylate gasoline is not degraded during the contacting of the at least the portion of the alkylate with the at least one molecular sieve.

17. The alkylation process according to claim 1, wherein the at least one olefin has from 2 to 5 carbon atoms and the at least one isoparaffin has 4 carbon atoms.

18. The alkylation process according to claim 9, wherein the at least one isoparaffin has 4 carbon atoms.

19. The alkylation process according to claim 16, wherein the at least one olefin has from 2 to 5 carbon atoms and the at least one isoparaffin has 4 carbon atoms.

20. The alkylation process according to claim 1, wherein, as analyzed by gas chromatography, the contacting causes no degradation of the alkylate gasoline.

21. The alkylation process according to claim 9, wherein, as analyzed by gas chromatography, the alkylate hydrocarbon product is not degraded.

22. The alkylation process according to claim 16, wherein, as analyzed by gas chromatography, the alkylate gasoline is not degraded.

23. The alkylation process according to claim 1, wherein the organic halide content of the alkylate prior to contacting is from 880 to 4000 ppm.

24. The alkylation process according to claim 9, wherein the organic halide content of the alkylate prior to contacting is from 880 to 4000 ppm.

25. The alkylation process according to claim 16, wherein the organic halide content of the alkylate prior to contacting is from 880 to 4000 ppm.

26. The alkylation process according to claim 9, wherein the contacting of the at least the portion of the alkylate produces the alkylate hydrocarbon product with the organic chloride content less than 10 ppm.

27. The alkylation process according to claim 1, wherein the contacting causes no degradation of the alkylate gasoline.

28. The alkylation process according to claim 1, wherein the organic halide absorption conditions include passing the at least the portion of the alkylate gasoline over the at least one molecular sieve at a linear hourly space velocity between 1 hr and 10 hr.

29. The alkylation process according to claim 9, wherein the organic halide absorption conditions include passing the at least the portion of the alkylate over the at least one molecular sieve at a linear hourly space velocity between 1 $hr^-$ and 10 $hr^-$.

30. The alkylation process according to claim 16, wherein the organic halide absorption conditions include passing the at least the portion of the alkylate over the at least one molecular sieve at a linear hourly space velocity between 1 $hr^-$ and 10 $hr^-$.

* * * * *